United States Patent [19]

Shimomura et al.

[11] Patent Number: 4,579,641
[45] Date of Patent: Apr. 1, 1986

[54] PH MEASUREMENT DEVICE

[75] Inventors: Takeshi Shimomura; Norihiko Ushizawa, both of Fujinomiya; Shuichiro Yamaguchi, Fuji; Tsutomu Murakami, Ueno, all of Japan

[73] Assignee: Terumo Kabushiki Kaisha, Tokyo, Japan

[21] Appl. No.: 749,189

[22] Filed: Jun. 26, 1985

[30] Foreign Application Priority Data

Jun. 30, 1984 [JP] Japan .................. 59-136340

[51] Int. Cl.⁴ ............................................. G01N 27/30
[52] U.S. Cl. .................... 204/403; 128/635; 204/415; 204/433; 324/438
[58] Field of Search .............. 204/433, 403, 400, 1 H, 204/415; 128/635; 324/438

[56] References Cited

U.S. PATENT DOCUMENTS 3,709,810  1/1973  Grubb et al. ............. 204/433 X
4,338,175  7/1982  Binder et al. ............. 204/433

Primary Examiner—G. L. Kaplan
Attorney, Agent, or Firm—Frishauf, Holtz, Goodman & Woodward

[57] ABSTRACT

A pH measurement device includes working and reference electrodes. The working electrode has a linear electrically conductive substrate, at least a distal end surface of which consists of platinum, and a selective hydrogen ion permeable layer formed on the distal end face of the substrate. The reference electrode includes an electric conductor formed to be insulated from the working electrode and surrounding the working electrode, a polymer-silver (I) complex layer formed on the outer circumferential surface of the conductor, and an ion-conductive layer containing an anionic compound and formed on the complex layer. The pH of a solution is measured in accordance with a difference between a potential of the working electrode and that of the reference electrode.

6 Claims, 4 Drawing Figures

PH MEASUREMENT DEVICE

BACKGROUND OF THE INVENTION

1. Field of the Invention

The present invention relates to a pH measurement device and, more particularly, to a device for measuring the pH of a solution by electrode potential response.

2. Description of the Prior Art

Current pH measurement devices widely use glass electrodes as indicator electrodes. However, a glass electrode requires a chamber for an internal reference solution and cannot be made small enough to be directly inserted into a vein of a subject. Measurement of the pH of a patient's body is important for diagnosis and prevention of various diseases. However, for this purpose, an indicator electrode or working electrode as a pH sensor and a reference electrode must be directly inserted into a portion of the patient's body which is to be measured, and the pH value of this portion must be measured with accuracy.

SUMMARY OF THE INVENTION

It is, therefore, an object of the present invention to provide a pH measurement device which can be rendered small enough to allow direct insertion into a patient's body and which can correctly measure the pH of a solution with accuracy.

In order to achieve the above object of the present invention, there is provided a pH measurement device comprising (A) a working electrode having a linear electrically conductive substrate, at least a distal end surface of which consists of platinum, and a selective hydrogen ion permeable film formed on the distal end surface of the substrate; and (B) a reference electrode, including an electric conductor formed to be insulated from the working electrode and surrounding the working electrode, a polymer-silver (I) complex layer formed on the outer circumferential surface of the conductor, and an ion-conductive layer containing an anionic compound and formed on the complex layer, wherein the pH of a solution is measured in accordance with a potential difference between a potential of the working electrode and that of the reference electrode.

The hydrogen ion permeable film preferably comprises a polymer derived from an electrooxidation polymerization of at least one aromatic compound selected from the group consisting of hydroxy aromatic compounds and nitrogen-containing aromatic compounds. An interference ion impermeable film which does not allow permeation of interference ions in the solution is preferably formed on the hydrogen ion permeable film.

Usually, the polymer-silver (I) complex layer comprises a complex of silver with a polymer having coordinating nitrogen atoms optionally added with a silver halide.

According to a particularly preferable aspect of the present invention, the ion-conductive film has a portion which extends from the polymer-silver (I) complex layer and has a distal end to be in contact with a solution to be measured. In this aspect, only the ion-conductive film of the reference electrode of the present invention is in contact with the solution so that the adverse influence of interfering ions (in particular, chlorine ions) can be eliminated. A water-insoluble heparin derivative layer is preferably formed on the interference ion impermeable layer. The heparin derivative increases an anti-thrombus property of the device.

DETAILED DESCRIPTION OF THE PREFERRED EMBODIMENTS

The preferred embodiment of the present invention will be described in detail with reference to the accompanying drawings.

Figure 1:
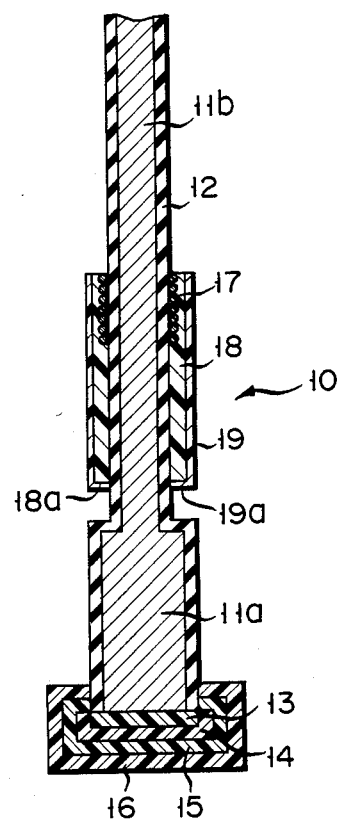
FIG. 1 is a schematic sectional view of a pH measurement device according to the present invention.

Referring to FIG. 1, a pH measurement device 10 of the present invention has a linear substrate 11a of an electrically conductive material, e.g., stainless steel. The linear substrate or substrate wire 11a has a diameter of, e.g., 0.05 to 0.5 mm. A lead wire 11b is connected to the substrate 11a by welding or the like. The substrate 11a and the lead wire 11b can consist of a single conductive wire. An insulating layer 12 of, e.g., Teflon is formed to surround the substrate 11a and the lead wire 11b. The insulating layer 12 can be formed by fitting a heat shrinkable insulating tube around the lead wire 11b and the substrate 11a and heating the tube.

A platinum layer 13 having a thickness of, e.g., 0.01 to 1 μm is formed on one exposed distal end surface of the substrate 11a by vapor deposition or sputtering.

A hydrogen ion permeable film 14 is formed on a surface of the platinum layer 13. The film 14 preferably comprises a polymer derived from an electrooxidation polymerization of at least one aromatic compound (monomer) selected from hydroxy aromatic compounds (e.g., phenol, 2,6- and 3,5-dimethylphenols, o-, m- and p-hydroxybenzophenones, o-, m- and p-hydroxybenzyl alcohols, 2, 2', 4, 4'-tetrahydroxybenzophenone, o-, m- and p-hydroxypropiophenones, o-, m- and p-hydroxybenzaldehydes, o-, m- and p-bensophenols, o-, m- and p-hydroxyanthraphenone, 4-(p-hydrophenyl)-2-butanone, and bisphenol A) and nitrogen-containing aromatic compounds (e.g., 1,2-diaminobenzene, aniline, 2-aminobenzotrifluoride, 2-aminopyridine, 2,3-diaminopyridine, 4,4'-diaminodiphenyl ether, 4,4'-methylenedianiline, N-(o-hydroxybenzyl)aniline pyrrole, 2,2-bis-(4-aminophenyl)hexafluoropropane, and 2,2-bis-[4-(4'-aminophenoxy)phenyl] hexafluoropropane). The layer 14 allows preferential permeation of hydrogen ions in a solution, particularly an aqueous solution, for pH measurement.

Electrooxidation polymerization of a selected aromatic compound can be performed as follows. A hydroxy aromatic compound and/or nitrogen-containing aromatic compound is dissolved at a concentration of, e.g., 1 mmol/liter to 0.5 mole/liter in an organic solvent (e.g., acetonitrile or methanol) containing a supporting electrolyte (e.g., sodium perchlorate or sodium hydroxide). The substrate 11a having the platinum layer 13 is immersed in the solution as a working electrode together with a reference electrode and a counter electrode. A predetermined constant voltage (usually, +1 V) with reference to the reference electrode is applied to the working electrode. The layer 14 usually has a thickness of 1 nm to 100 μm.

The working electrode of the pH measurement device can be constituted only by the substrate 11a, the platinum layer 13 and the layer 14. However, in order to prevent permeation of interference ions (ions other than hydrogen ions) in the solution for pH measurement, an interference ion impermeable layer 15 is preferably formed on the layer 14. The layer 15 can be formed by, for example, sputtering polycarbonate. The layer 15 is permeable to hydrogen ions and usually has a thickness of 10 nm to 100 μm.

When the pH measurement device of the present invention is used to measure the pH value of blood, in order to prevent coagulation of blood, a layer 16 of a water-insoluble heparin derivative is preferably formed on the layer 15. The heparin derivative can be obtained by reacting heparin with benzalkonium chloride (surfactant having quaternarized methyl groups). Heparin is reacted with benzalkonium chloride such that substantially all of the sulfonic acid groups reacts with benzalkonium chloride.

The reference electrode of the pH measurement device of the present invention includes an electric conductor 17 obtained by winding a conductive wire, in particular, a silver wire having a diameter of, e.g. 0.05 to 0.5 mm around the insulating layer 12. A polymer-silver (I) complex layer 18 is formed around the outer circumferential surface of the conductor 17. The polymer-silver (I) complex is obtained by dissolving a film-forming polymer (e.g., polyacrylonitrile, polyacrylamide, polyvinylamine, or polymethacrylonitrile) containing an atom or atoms capable of coordinating with silver ion (e.g., nitrogen atom) and an inorganic silver salt such as silver nitrate in an organic solvent such as dimethyl formamide (DMF), and casting the resultant solution around the conductor 17. The layer 18 may contain a silver halide such as silver chloride.

An ion-conductive film 19 containing an anionic compound and having a thickness of, e.g., about 100 μm to 20 mm is formed on the layer 18. The film 19 can be made of a polyanion such as polystyrene sulfonic acid, polyacrylic acid, polymethacrylic acid, or poly(perfluorosulfonic acid). Poly(perfluorosulfonic acid) is available as "Nafion" from du Pont de Nemours. An anionic compound as enumerated above produces an ion complex with silver ions to prevent elution of the ions. When interfering ions (in particular, chlorine ions) are present in an amount enough to influence the electromotive force in the solution the pH of which is to be measured, the film 19 serves to prevent permeation of such interfering ions. Preferably, the film 19 extends from the layer 18 as shown at 19a in FIG. 1. In other words, the film 19 covers the layer 18 also at the end face 18a thereof. With this construction, the reference electrode of the pH measurement device according to the present invention contacts the solution only at the film 19, and thus the influence of interfering ions, particularly chlorine ions, can be eliminated.

The reference electrode is preferably coated with an insulating layer such as Teflon layer or a heat-shrinkable tube (not shown) such as a polyolefin resin tube for providing protection.

When the pH of a solution is measured using the pH measurement device of the present invention, the device is immersed in the solution to a level such that the film 19 contacts the solution. In this state, the potential difference between the reference and working electrodes is measured using a potentiometer connected to the lead 11b and the wire 17. The measured potential difference is used to determine the pH of the solution based on a pH value potential calibration curve which has been obtained beforehand.

The present invention will now be described by way of its examples.

EXAMPLE 1

A stainless steel (JIS SUS 304) wire having a diameter of 0.5 mm was insulated on its outer circumferential surface with a fluororesin (trade name: "Teflon"). The exposed distal end of the SUS wire was polished with silicon carbide paper (about 8.0 μm particle size) and alumina powder (0.3 μm particle size). After washing with water and methanol, the SUS wire was dried. A thin platinum film was formed by sputtering on the polished surface of the wire at power of 200 W and an irradiation time of 15 seconds to obtain an electrode base. The platinum film had a thickness of 0.056 μm. A magnetron diode discharge apparatus was used for sputtering.

A film of an electrolytic oxidation copolymer of phenol and 1,2-diaminobenzene was formed on the surface of the thin platinum film by electrolytic oxidation polymerization. For polymerization, a conventional three-compartment cell was used, a platinum net electrode was used as a counter electrode, a saturated sodium chloride calomel electrode (SSCE) was used as a reference electrode, and the electrode base was used as a working electrode. Each electrode was used after being washed with distilled water and dried. The electrolytic solution used was a methanol solution containing 5 mM of phenol, 5 mM of 1,2-diaminobenzene and 30 mM of sodium hydroxide. The electrolytic solution was well deoxidized before electrolysis. After scanning an applied voltage and confirming that oxidation of both the monomers was occurring at the platinum surface, the applied voltage was held at +1.0 V (vs. SSCE), and electrolysis was performed for 3 minutes to deposit the desired polymeric substance on the platinum surface to a thickness of 0.05 μm. Formation of the polymeric film was confirmed by a cyclic voltammogram. A thin polycarbonate film of 0.03 μm thickness was coated on the polymeric thin film by sputtering, thus preparing a desired working electrode.

A Teflon-coated SUS wire having a diameter of 0.2 mm was spot-welded to the SUS wire of the working electrode and used as a lead wire. The assembly thus obtained was placed in a Teflon tube (9 cm length × 0.25 cm outer diameter), and the tube was sealed. Then, as shown in FIG. 1, a silver wire (0.2 mm diameter) was spirally wound, and a layer of a polyacrylonitrile (PAN)-silver ion complex was formed to a thickness of 0.15 mm. The complex layer was formed by mixing silver nitrate (30% by weight concentration) in a 3% by weight PAN solution in DMF and casting the solution on the silver wire.

In order to stabilize and densify the complex layer, submersion of the assembly in a saturated silver nitrate solution in methanol was repeated. Subsequently, a Nafion film (polyperfluorosulfonic acid film; available from du Pont de Nemours) was fitted around the assembly in a cylindrical form (110 mm length × 1.8 mm inner diameter). A heat shrinkable tube (polyolefin resin) was fitted therearound for fixing. Thus, a linear composite electrode (pH measurement device of the present invention) was prepared.

A catheter sheath introducer (having an outer diameter of 5 Fr (French; about 1.7 mm); available from USA Cordis Inc.) was inserted into the jugular vein of a rabbit. The composite electrode was inserted into the introducer and the pH value of blood was directly measured. Changes in electromotive force (electrode potential at equilibrium) between the working and reference electrodes of the composite electrode of the present invention were examined. When measurement was continued for 3 hours, the working electrode potential was constant at about $-260$ mV$\pm 2$ mV with reference to the PAN-Ag$^+$/Ag reference electrode (see point C in FIG. 2). The electrode potential became constant with a deviation of $\pm 2$ mV about 3 minutes (response time) after start of measurement.

For blood sampled at 20 seconds, 15 minutes, 30 minutes, 60 minutes, 90 minutes, 120 minutes, 150 minutes, and 180 minutes after start of measurement, the pH value was 7.352 to 7.373, $P_{CO_2}$ ($CO_2$ partial pressure) was 30.0 to 34.4 mmHg, and $P_{O_2}$ ($O_2$ partial pressure) was 38.2 to 41.8 mmHg. Each measurement value was obtained with a blood analyzer (BMS-MK-2 type; available from Radiometer Inc.)

The relationship between the working electrode potential at equilibrium (mV) measured by the device of this Example and the pH value (measured by a commercially available pH meter) was examined using standard serum. A linear relationship satisfying the Nernst's relation shown in FIG. 2 (line B) was obtained. The working electrode potential at equilibrium at a pH of 7.40 was $-265$ mV with reference to the PAN-Ag$^+$/Ag reference electrode (measuring temperature 37° C.$\pm 0.1$° C.). Since the equilibrium potentials both in the whole blood and the blood serum were the same, the pH value in blood can be determined using the calibration curve in serum prepared according to the present invention. The standard serum used was obtained by adjusting the pH of Versatol-A (General Giagostic Der Warner. Lambert.) with phosphoric acid buffer solution to a concentration of 20%.

Figure 2:
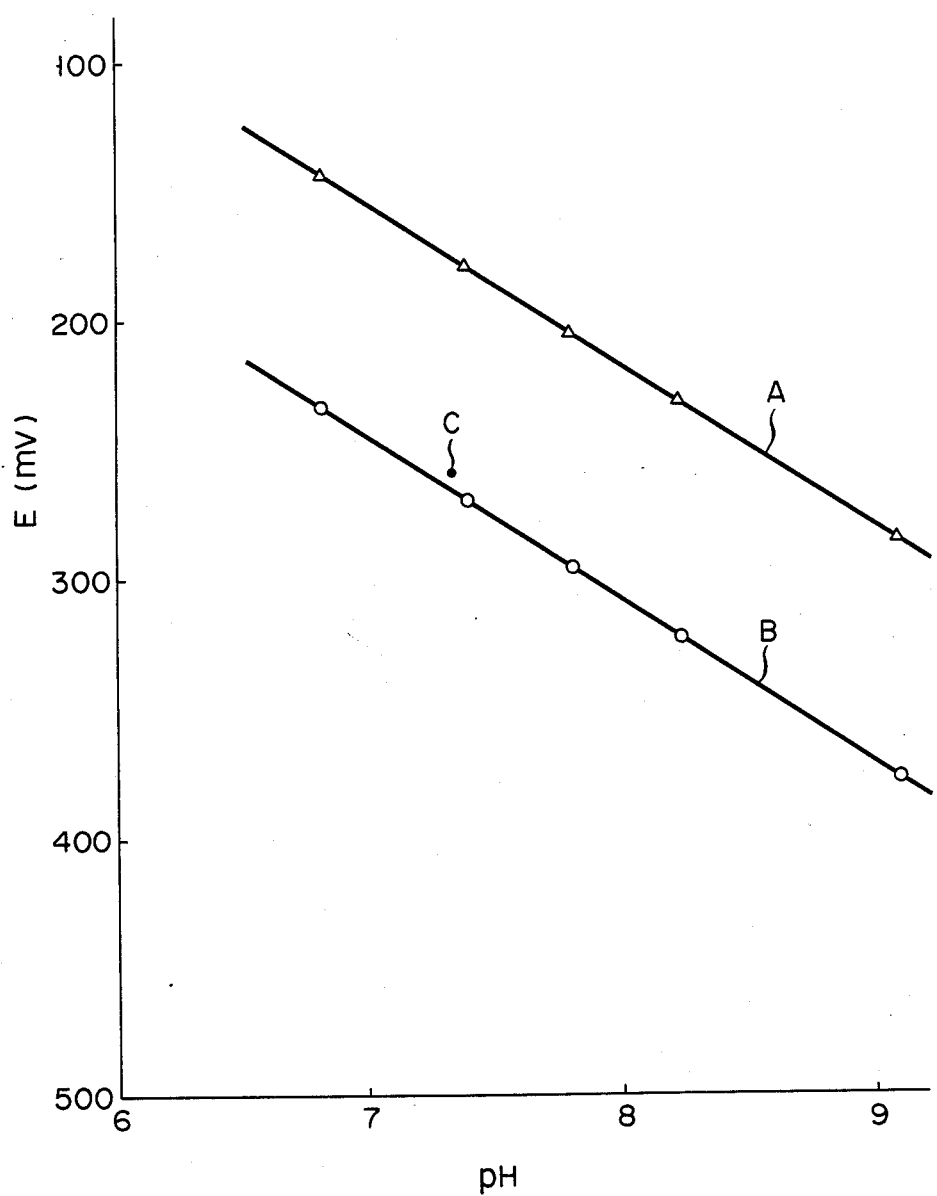
FIGS. 2 to 4 are graphs showing the characteristics of the pH measurement device according to the present invention.

The relationship between the pH and the electrode potential at equilibrium of the working electrode of the present invention in 0.05 M phosphoric acid buffer solution is as indicated in FIG. 2 (line A). It can be seen from this graph that the electrode potential at equilibrium is $-180$ mV at pH of 7.40, and a change in electrode potential at equilibrium per unit pH value is $-61$ mV/pH ($6.6 \leq$ pH $\leq 9.1$) (measurement temperature: 37° C.).

EXAMPLE 2

The same test as in Example 1 was performed using an agar salt bridge as a reference electrode and using a silver/silver chloride electrode. It took up to 3 minutes before a stable working electrode potential at equilibrium was obtained within a potential deviation of $\pm 2$ mV. Continuous pH measurement of rabbit blood was performed for 3 hours at the vein side and 3 hours at the artery side (connected to the vein with a shunt of about 3 cm length). The working electrode potential at equilibrium was about 194 mV at the vein side, and 180 mV with reference to Ag/AgCl reference electrode at the artery side (points C in FIG. 3).

Figure 3:
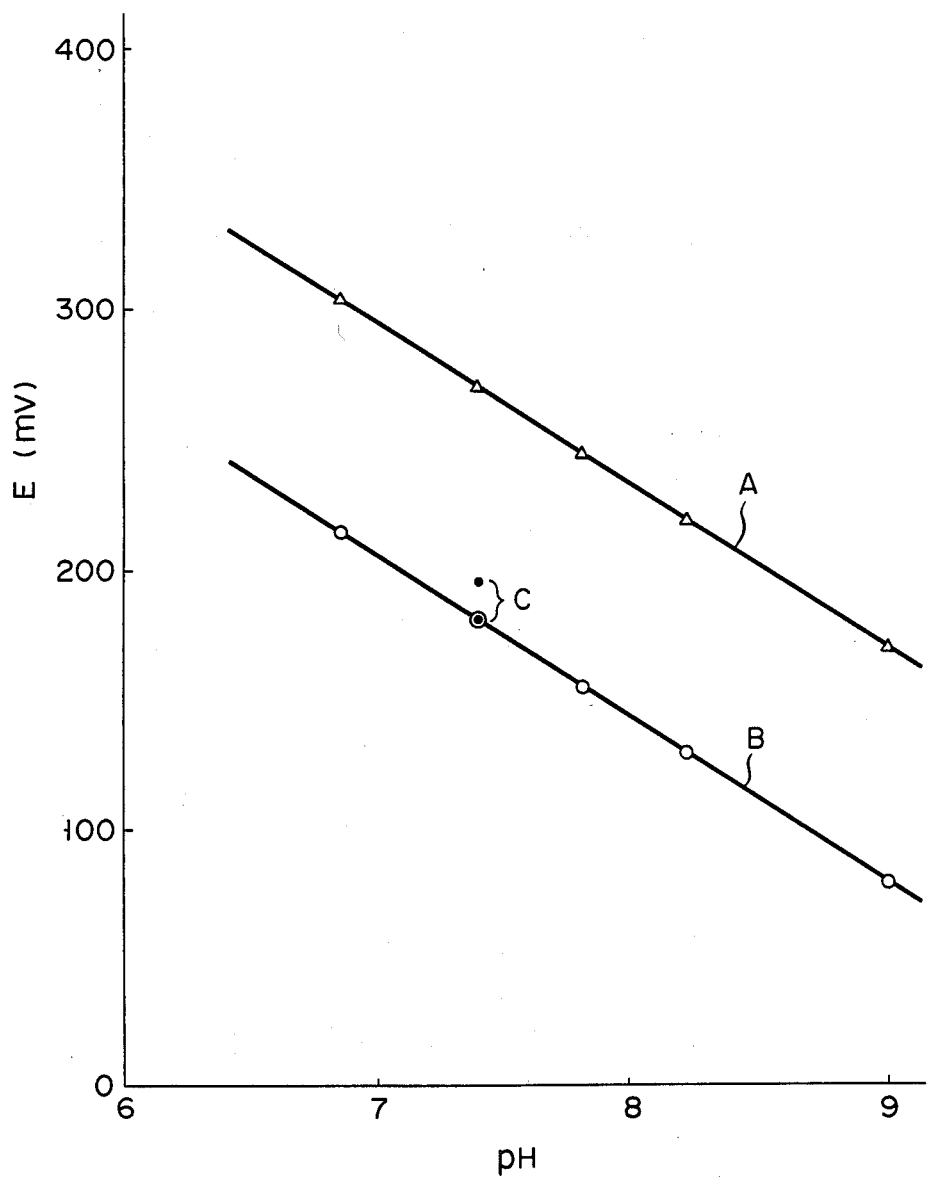

This potential is the same as the potential of 180 mV at the pH of 7.4 in standard serum indicated in FIG. 3 (line B). Therefore, the pH of blood can be determined from the relationship between the pH and the electrode potential at equilibrium shown in FIG. 3. For the purpose of comparison, a working electrode potential at equilibrium at a pH of 7.4 in a standard buffer solution was 270 mV with reference to Ag/AgCl (37° C.).

After measurement was started, about 0.5 ml of whole blood was sampled, and was subjected to measurement by a blood analyzer. Immediately after starting measurement, then 5 minutes, 10 minutes, 60 minutes, 90 minutes, 120 minutes, and 180 minutes thereafter, the pH was 7.391 to 7.437, $P_{CO_2}$ was 29.7 to 34.4 mmHg, $P_{O_2}$ was 51.0 to 67.1 mmHg for the venous blood. Within a time range between 180 minutes and 300 minutes after start of measurement, the pH was 7.384 to 7.433, $P_{CO_2}$ was 30.3 to 34.8 mmHg, and $P_{O_2}$ was 51.0 to 69.1 mmHg (artery blood).

EXAMPLE 3

Heparin, 200,000 units, was reacted (ion bonded) with 2.47 g of benzalkonium chloride in an ethanoldichloromethane mixture to produce a heparin complex (water-insoluble heparin derivative), which was filtered, washed with water, and dried.

The same procedure was followed as in Example 1 except that the heparin complex was coated on a polycarbonate surface of the working electrode of Example 1 to provide a desired pH measurement device. The pH of jugular vein blood of a rabbit was measured, using the device.

A catheter sheath introducer having an outer diameter of 5 Fr (Cordis Inc.) was inserted into the jugular vein of a rabbit, and the device of this Example was inserted into the introducer to directly measure the pH value of blood. When changes in electrode potential at equilibrium between the electrodes were examined, the working electrode potential was measured to be $-230$ mV after 2.5 hours of continuous measurement (point C in FIG. 4).

The pH value during potential measurement was measured to be 7.391 to 7.412 by a blood analyzer (BMS-MK-2 type; available from Radiometer Inc.). The $P_{CO_2}$ was 32.5 to 39.5 mmHg, and $P_{O_2}$ was 43.6 to 52.8 mmHg.

Figure 4:
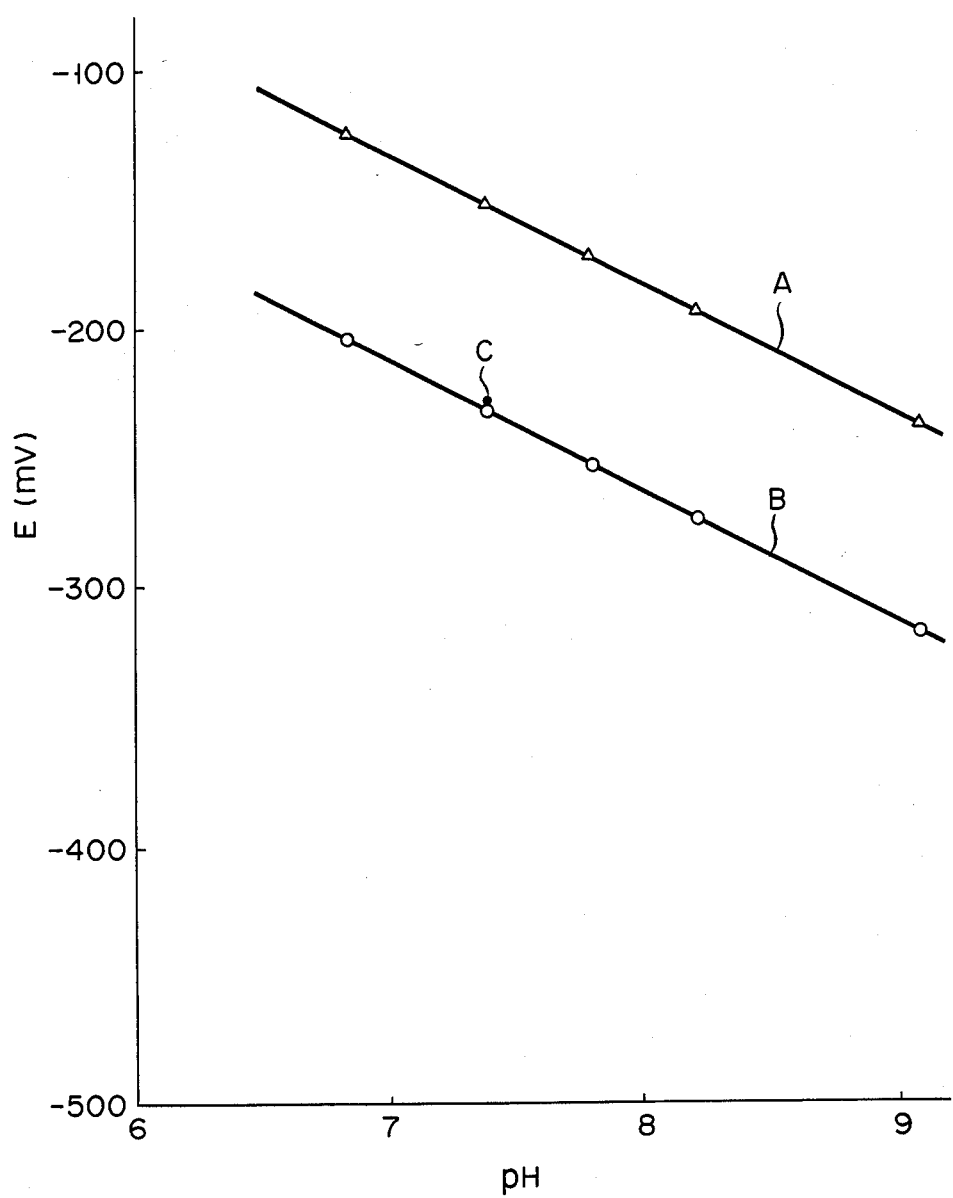

The relationship between the working electrode potential at equilibrium (mV) measured by the device of the present invention and the pH in standard serum (Veratol A) was examined as in Example 1. A linear relationship was obtained (line B in FIG. 4). The working electrode potential at equilibrium at a pH of 7.40 was $-235$ mV with reference to the reference electrode (at $37\pm 0.1$° C.). For comparison, the working electrode potential at equilibrium in a 0.05 M phosphate buffer solution was $-164$ mV (7.40 pH) as shown in FIG. 4 (line A). Change in electrode potential (at equilibrium) per unit pH value was $-52$ mV/pH (37° C.).

An in vivo test was performed using an agar salt bridge (silver/silver chloride) as a reference voltage. It took about 5 hours or less before a stable electrode potential at equilibrium was obtained, and the electrode potential at equilibrium was $180\pm 2$ mV with reference to the Ag/AgCl reference electrode. In the same manner as described above, the pH value corresponding to a potential of 180 mV was determined to be 7.38 (37° C.) from the relationship between the working electrode potential at equilibrium (mV) and the pH in standard serum.

The in vivo pH can be determined using the above calibration curve.

The pH value during potential measurement was determined to be 7.297 to 7.386, $P_{CO_2}$ was 35.7 to 38.1 and $P_{O_2}$ was 37.7 to 38.7 by a blood analyzer (the same as that used in Example 2).

EXAMPLE 4

The pH measurement of the jugular vein blood in vivo (animal: rabbit) was performed following the same procedures as in Example 3, by using a pH measurement device prepared in the same manner as in Example 3 except that an electrolytic oxidation polymerized 2,2′,4,4′-tetrahydroxybenzophenone (THBP) was used in place of the oxidation copolymerized film of Example 3. The response time was within 5 minutes and sufficiently short. The working electrode potential at equilibrium was $-360$ mV $\pm 2$ mV with reference to the reference electrode and remained constant. However, the potential was subject to influence by components in the blood within about one hour.

The device of this Example could measure pH of a phosphoric acid standard buffer solution containing chlorine ions at a concentration of $10^{-3}-1$ M (mole/l) without being influenced by the chlorine ions.

With the device of this Example, pH measurement cannot be performed in systems such as blood in which proteins and active substances are coexistent but pH measurement can be performed when ions such as chlorine ions are coexistent in addition to hydrogen ions.

As described above, the pH measurement device of the present invention can be rendered small enough so that it can be directly inserted into a living body and can measure the pH with high precision.

What is claimed is:

1. A pH measurement device comprising
   (A) a working electrode having a linear electrically conductive substrate, at least a distal end surface of which consists of platinum, and a selective hydrogen ion permeable layer formed on the distal end surface of the substrate; and
   (B) a reference electrode including an electric conductor formed to be insulated from the working electrode and surrounding the working electrode, a polymer-silver (I) complex layer formed on the outer circumferential surface of the conductor, and an ion-conductive layer containing an anionic compound and formed on the complex layer, wherein the pH of a solution is measured in accordance with a potential difference between a potential of the working electrode and that of the reference electrode.

2. A device according to claim 1, wherein said hydrogen ion permeable layer comprises a polymer derived from an electrooxidation polymerization of at least one aromatic compound selected from the group consisting of hydroxy aromatic compounds and nitrogen-containing aromatic compounds.

3. A device according to claim 1, wherein said polymer-silver complex layer comprises a complex of silver with a polymeric compound having a coordinating nitrogen atom, or a mixture of the complex with a silver halogenide.

4. A device according to claim 3, wherein said ion-conductive layer constitutes a portion which extends from said polymer-silver complex layer and has a distal end which is to be brought into contact with the solution.

5. A device according to claim 1, further comprising an interference ion impermeable layer formed on said hydrogen ion permeable layer.

6. A device according to claim 5, further comprising a layer of a water-insoluble heparin derivative formed on said interference ion impermeable layer.

* * * * *